United States Patent
Rabinovich-Guilatt et al.

(10) Patent No.: US 9,220,694 B2
(45) Date of Patent: *Dec. 29, 2015

(54) EMULSION COMPOSITIONS CONTAINING CETALKONIUM CHLORIDE

(71) Applicant: NOVAGALI PHARMA SA, Evry (FR)

(72) Inventors: Laura Rabinovich-Guilatt, Kadima (IL); Gregory Lambert, Chatenay Malabry (FR); Frederic Lallemand, Fresnes (FR); Betty Philips, Antony (FR)

(73) Assignee: SANTEN SAS, Evry (FR)

( * ) Notice: Subject to any disclaimer, the term of this patent is extended or adjusted under 35 U.S.C. 154(b) by 191 days.

This patent is subject to a terminal disclaimer.

(21) Appl. No.: 13/957,621

(22) Filed: Aug. 2, 2013

(65) Prior Publication Data

US 2013/0337019 A1   Dec. 19, 2013

Related U.S. Application Data

(63) Continuation-in-part of application No. 13/096,512, filed on Apr. 28, 2011, now Pat. No. 8,524,779, which is a continuation of application No. 11/829,428, filed on Jul. 27, 2007, now Pat. No. 7,973,081, which is a continuation-in-part of application No. 11/494,493, filed on Jul. 28, 2006, now abandoned.

(30) Foreign Application Priority Data

Jul. 28, 2006 (EP) ........................ 06291236
Jul. 9, 2007 (EP) ........................ 07112097
Jul. 10, 2007 (WO) ................ PCT/IB2007/053441

(51) Int. Cl.
*A61K 9/107* (2006.01)
*A61K 9/00* (2006.01)
*A61K 38/13* (2006.01)
*A01N 33/12* (2006.01)
*A01N 25/04* (2006.01)
*A01N 25/30* (2006.01)
*A61K 31/14* (2006.01)
*A61K 31/765* (2006.01)
*A61K 47/18* (2006.01)
*A61L 12/14* (2006.01)
*C07C 211/63* (2006.01)

(52) U.S. Cl.
CPC ............. *A61K 31/14* (2013.01); *A61K 9/0014* (2013.01); *A61K 9/0048* (2013.01); *A61K 9/107* (2013.01); *A61K 31/765* (2013.01); *A61K 38/13* (2013.01); *A61K 47/186* (2013.01); *A61L 12/143* (2013.01); *C07C 211/63* (2013.01)

(58) Field of Classification Search
None
See application file for complete search history.

(56) References Cited

U.S. PATENT DOCUMENTS

| | | |
|---|---|---|
| 3,954,644 A | 5/1976 | Krezanoski et al. |
| 5,188,826 A | 2/1993 | Chandrasekaran et al. |
| 5,190,936 A | 3/1993 | Laugier et al. |
| 5,435,998 A | 7/1995 | Abelson |
| 5,496,811 A | 3/1996 | Aviv et al. |
| 5,588,559 A | 12/1996 | Vallet mas et al. |
| 5,698,219 A | 12/1997 | Valdivia et al. |
| 5,767,153 A | 6/1998 | Bowman et al. |
| 5,951,988 A | 9/1999 | Little-van den Hurk et al. |
| 6,007,826 A | 12/1999 | Benita et al. |
| 6,030,789 A | 2/2000 | Ward et al. |
| 6,114,319 A | 9/2000 | Kimura et al. |
| 6,375,936 B1 | 4/2002 | Allard et al. |
| 6,635,676 B2 | 10/2003 | Baker, Jr. et al. |
| 6,656,460 B2 | 12/2003 | Benita et al. |
| 6,677,304 B2 | 1/2004 | Di Napoli |
| 6,872,705 B2 | 3/2005 | Lyons |
| 6,953,776 B2 | 10/2005 | Di Napoli |
| 2002/0169138 A1 | 11/2002 | Kunz et al. |
| 2003/0092612 A1 | 5/2003 | Lyons |
| 2003/0108626 A1 | 6/2003 | Benita et al. |
| 2003/0165545 A1 | 9/2003 | Huth et al. |
| 2005/0059583 A1 | 3/2005 | Acheampong et al. |
| 2005/0059644 A1 | 3/2005 | Rood et al. |
| 2005/0158349 A1 | 7/2005 | Jampani et al. |
| 2005/0175651 A1 | 8/2005 | Simonnet et al. |

(Continued)

FOREIGN PATENT DOCUMENTS

| | | |
|---|---|---|
| EP | 0642782 | 3/1995 |
| EP | 0878197 A1 | 11/1998 |

(Continued)

OTHER PUBLICATIONS

Choi et al., "Low toxicity of cationic lipid-based emulsion for gene transfer," Biomaterials, 2004, vol. 25, pp. 5893-5903.
Grant et al., "Prolonged Adverse Effects of Benzalkonium Chloride and Sodium Dodecyl Sulfate in a Primary Culture System of Rabbit Corneal Epithelial Cells," Fundamental and Applied Toxicology, 1996, vol. 33, No. 1., pp. 71-82.
Ogawa et al., "Production and Characterization of O/W Emulsions Containing Cationic Droplets Stabilized by Lecithin-Chitosan Membranes," J. Agric. Food Chem., 2003, vol. 51, pp. 2806-28012 and vol. 51, 2003, pp. 5522-5527.

(Continued)

*Primary Examiner* — Kevin S Orwig
(74) *Attorney, Agent, or Firm* — Young & Thompson

(57) ABSTRACT

Compositions containing quaternary compounds in which the nitrogen atom is substituted by at least one alkyl group having at least 12 carbon atoms, and the composition includes at least 20% in weight by weight of the total composition, of ammonium halides in which the nitrogen atom is substituted by at least one alkyl group having at least 14 carbon atoms and more than 5%, preferably more than 7% in weight by weight of the total composition, of ammonium halides in which the nitrogen atom is substituted by at least one alkyl group having at least 16 carbon atoms. Also, ophthalmic oil-in-water emulsions containing such compositions, the ophthalmic emulsions being useful for eye care or for the treatment of eye conditions.

18 Claims, 3 Drawing Sheets

(56) References Cited

U.S. PATENT DOCUMENTS

| | | |
|---|---|---|
| 2006/0002963 A1 | 1/2006 | Rabinovich-Guilatt et al. |
| 2006/0100288 A1 | 5/2006 | Bague et al. |
| 2006/0257426 A1 | 11/2006 | Baker et al. |
| 2007/0231406 A1 | 10/2007 | Bucalo et al. |
| 2007/0248645 A1 | 10/2007 | Bague et al. |
| 2008/0025941 A1 | 1/2008 | Rabinovich-Guilatt et al. |
| 2008/0107738 A1 | 5/2008 | Philips et al. |
| 2008/0268020 A1 | 10/2008 | Philips et al. |
| 2008/0279949 A1 | 11/2008 | Merisko-Liversidge et al. |
| 2009/0018057 A1 | 1/2009 | Lambert et al. |

FOREIGN PATENT DOCUMENTS

| | | |
|---|---|---|
| EP | 1611879 A1 | 1/2006 |
| EP | 1655021 | 5/2006 |
| GB | 633175 | 12/1949 |
| JP | 1993-116286 A | 10/1994 |
| JP | 2005-206598 A | 8/2005 |
| JP | 2005523261 | 8/2005 |
| JP | 2006001948 | 1/2006 |
| WO | 93-18852 A1 | 9/1993 |
| WO | 9531956 | 11/1995 |
| WO | 9531958 | 11/1995 |
| WO | 9531966 | 11/1995 |
| WO | 9725975 | 7/1997 |
| WO | 9825620 | 6/1998 |
| WO | 99-51763 A1 | 10/1999 |
| WO | 0018316 | 4/2000 |
| WO | 0122936 | 4/2001 |
| WO | 03-006046 A1 | 1/2003 |
| WO | 03-053405 A1 | 7/2003 |
| WO | 03063826 | 8/2003 |
| WO | 2006050836 | 5/2006 |

OTHER PUBLICATIONS

Ott et al., "A Cationic sub-micron emulsion (MF59/ DOTAP) is an effective delivery system for DNA vaccines," J Control Release, vol. 79, 2002, pp. 1-5.

Nielloud et al., Drugs and the Pharmaceutical Sciences, Pharmaceutical emulsions and suspensions, Marcel Dekker, 2000, vol. 105, pp. 6-7.

Pignatello et al., "Flurbiprofen-loaded acrylate polymer nanosuspensions for opthalmic application," Biomaterials, 2002, vol. 23, pp. 3247-3255.

Tamilvanan et al., "The potential of lipid emulsion for ocular delivery of lipophilic drugs," European Journal of Pharmaceutics and Biopharmaceutics, 2004, vol. 58, No. 1, pp. 357-368.

Ward et al., "Evaluation of Chemically Induced Toxicity Using an in Vitro Model of Human Corneal Epithelium," Toxicology in vitro, 1997, vol. 11, No. 1-2, pp. 121-139.

Household Products Database entry for Mineral Oil accessed Jul. 7, 2010 at http://householdproducts.nlm.nih.gov/cgibin/household/brands?tbl=chem&id =227.

Robiot, Cetalkonium Chloride Product Info., copyright 2003, p. 1.

Generic Name Latanoprost, MedicineNet.com, Jul. 23, 1998, pp. 1-2.

Gershenovich et al., "The Physical, Chemical and Biomedical Properties of Benzalkonium Chloride", Khimicheskaya Promyshlennost ,1981, vol. 3, pp. 143-145.

Adriaens et al., "The mucosal toxicity of different benzalkonium chloride analogues evaluated with an alternative test using slugs", Pharmaceutical Research, 2001, vol. 18, No. 7, pp. 937-942.

EMULSION COMPOSITIONS CONTAINING CETALKONIUM CHLORIDE

FIELD OF INVENTION

This invention relates to pharmaceutical, ophthalmic or cosmetic compositions containing quaternary ammonium compounds, more preferably to ophthalmic emulsions being useful for eye care or for the treatment of eye conditions. This invention also relates to compositions including at least one quaternary ammonium compound as cationic agent.

BACKGROUND OF INVENTION

Quaternary ammonium compounds are organic compounds usually used as an antiseptic or antimicrobial agent. For example, benzalkonium chloride is a nitrogenous cationic surface-acting agent belonging to the quaternary ammonium group. Benzalkonium chloride is generally defined as a mixtures of compounds of general formula C6H5CH2N(CH3)2RC1, wherein R is a C12-C24 alkyl group.

Benzalkonium chloride, as usually provided by the manufacturers wanting to comply with the European and/or American Pharmacopeia, is a mixture of n-alkyl dimethyl benzyl ammonium chlorides of various alkyl chain lengths. For example, FeF Chemicals A/S (Denmark) supplies, under reference 8100301U (BAK USP/NF), a mixture of three alkyl dimethyl benzyl ammonium chlorides including: (1) 60-70% of C12-alkyl dimethyl benzyl ammonium chloride (2) 30-40% of C14-alkyl dimethyl benzyl ammonium chloride, and less than 5% of C16-alkyl dimethyl benzyl ammonium chloride.

Benzalkonium chloride, as a mixture of alkyl dimethyl benzyl ammonium having various alkyl chain lengths is used as preservative agent in topical ophthalmic products.

Benzalkonium chloride also has cationic agent properties, and was used as cationic agents for emulsions, especially ophthalmic emulsions.

When mixtures of benzalkonium chlorides having various alkyl chain lengths are used in emulsions, they may act both as preservative agents and cationic agents.

The Applicant worked on long chain quaternary ammonium compounds, and noticed that the length of the alkyl chain was important with regards to the function performed by the quaternary ammonium compounds, i.e. cationic agent and/or preservative agent.

Acting on the length of the alkyl chain resulted in enhancing or reducing the cationic power of the quaternary ammonium compounds. Without wanting to be linked by any theory, the Applicant observed on working on oil-in-water emulsions, that long chain quaternary ammonium compounds are preferentially localized at the oil/water interface of the emulsions, resulting in emulsions with higher zeta potential and consequently, more stable emulsions. As quaternary ammonium may be considered as undesirable or toxic, it is thus a goal of this invention to provide cationic composition having a reduced content of quaternary ammonium compound.

The Applicant also observed that, in emulsions, quaternary ammonium compounds having long alkyl chains, for example quaternary ammonium compounds having C14-C18 alkyl chains, when compared to C12-alkyl chains, did not have a good bactericidal activity, whereas they conferred a greatest cationic power.

Moreover, the Applicant observed that long chain quaternary ammonium compounds were present preferentially at the oil/water interface of the emulsion droplets, and less in the aqueous phase. The fact that quaternary ammonium compounds may be present in the aqueous phase in a very small amount only, or not present, leads to a loss of preservative effect or poor preservative effect, as well as to less toxic emulsions.

Thus, one of the goals of this invention is to provide stable cationic emulsions comprising a reduced amount of benzalkonium chlorides, and still using said benzalkonium chlorides as a source, or the only source, of cationic agents, said emulsions being preserved or not.

Another goal of the present invention is to provide emulsions that are not toxic, even if they comprise quaternary ammonium compounds.

Preferably, the emulsions of the invention are useful for ophthalmic purposes.

Therefore, the present invention aims at providing a stable and non-toxic cationic emulsion comprising quaternary ammonium compounds as cationic agents. As quaternary ammonium compounds may be considered as being toxic when ophthalmologically used, their amount should thus be reduced, while retaining stability.

It was surprisingly found by the Applicant that ammonium halides having longer alkyl chain provide more stable and less toxic emulsions, even when used in limited amounts. Especially, CKC provided astounding good results with this regard, as demonstrated in the example part.

DEFINITIONS

In the meaning of this invention,

"Cationic emulsions" are emulsions having a positive zeta potential, preferably a zeta potential higher to 10 mV;

"alkyl" means a saturated or unsaturated hydrocarbon chain;

"long alkyl chain" are alkyl moieties having at least 12 carbon atoms;

"quaternary ammonium compounds" refer to ammonium halides in which the nitrogen atom is substituted by only one or at least one alkyl group having at least 12 carbon atoms; quaternary ammonium compounds also, but not exclusively, include n-alkyl dimethyl benzyl ammonium chloride also called benzalkonium chloride (hereinafter also referred to as BAK or ADBAC); n-alkyl dimethyl benzyl ammonium bromide; n-alkyl trimethyl ammonium bromide (also referred to as ATAB), n-alkyl meaning an alkyl group of at least 12 carbon atoms;

"C14-alkyl ammonium halides" means ammonium halides in which the nitrogen atom of the ammonium group is substituted by at least one alkyl group having at least 14 carbon atoms;

"BAK C12" refers to benzododecinium chloride (CAS 139-07-1);

"BAK C14" refers to myristalkonium chloride (CAS 139-08-2);

"BAK C16" refers to cetalkonium chloride or CKC(CAS 122-18-9);

"ATAB C12" refers to lauryl trimethyl ammonium bromide (CAS1119-94-4);

"ATAB C14" refers to Myristil trimethyl ammonium bromide (CAS 1119-97-7);

"ATAB C16" or "CTAB" refers to Cetyl trimethyl ammonium bromide (CAS 57-09-0);

"MCT" means Medium chain triglycerides; for the experimentation, Mygliol 812 (Sasol, Germany) was the MCT used;

"ND" means "not determined".

DETAILED DESCRIPTION

The invention relates to a cationic oil-in-water emulsion comprising an ammonium halide composition as cationic agent. The ammonium halide composition includes in a preferred embodiment only one ammonium halide, which is C16-alkyl quaternary ammonium halide.

The oil-in-water emulsion of the invention presents the advantages to be very stable and non-toxic, compared to emulsions comprising benzalkonium chlorides. By cationic oil-in water emulsion is understood an oil-in-water emulsion having a positive zeta potential. The emulsion of the invention has a positive zeta potential and is stable, which means that it keeps a positive zeta potential overtime.

In a preferred embodiment, the oil-in-water emulsion according to the invention includes droplets of size 100 to 500 nm, preferably 200 to 300 nm.

In a preferred embodiment, the oil-in-water emulsion of the invention is useful for eye care or for the treatment of eye diseases or eye conditions.

In a preferred embodiment of the present invention, eye diseases or eye conditions means a dry eye condition.

A diminution of the quantity of tears produced and distributed through the lacrimal ducts or a decrease in the stability of the tear film produced, results in a condition of the eye referred to as dry eye. Dry eye conditions act to decrease visual acuity, produce discomfort, ranging from mild to intense and eventually, if allowed to remain untreated and uncorrected, result in permanent damage with degradation of the exposed ocular tissues, with a complete breakdown of corneal tissue necessitating, in the extreme, corneal transplants.

The symptoms associated with dry eye are often exacerbated with subjects using contact lens.

A dry eye condition in this context therefore refers to dry eye accompanying lacrimal fluid reduction, tear deficiency, xerosis of the eye, Sjogren's syndrome, keratoconjunctivitis sicca (KCS), atopic keratoconjunctivitis sicca (AKC), vernal keratoconjunctivitis (VKC), Stevens-Johnson syndrome, pemphigoid of the eye, marginal blepharitis, failure in eyelids closure, or sensory nerve numbness, dry eye accompanying allergic conjunctivitis, dry eye after viral conjunctivitis, dry eye after cornea surgery including laser in situ keratomileusis (LASIK), dry eye after cataract surgery, dry eye associated with contact lens wearing, or dry eye associated with VDT tasks.

More preferably, the oil-in-water emulsion according to the invention comprises:
- a) an oil phase,
- b) 0.0005% to 0.1% w/w preferably 0.001% to 0.02% w/w of the weight of the emulsion of a composition of ammonium halides according to the invention, as described hereabove, to the weight of the emulsion,
- c) surfactants,
- d) optionally antioxidants, tonicity, viscosifying, pH adjusting, buffering, preservative, solubilizers, chelating or thickener agents,
- e) water.

In an embodiment of the present invention, said composition of ammonium halides comprises at least one ammonium quaternary ammonium halide, in which the nitrogen atom of the ammonium group is substituted by only one or at least one alkyl group having at least 12 carbon atoms, said composition including:
- at least 20% in weight by weight of the total composition of ammonium halides in which the nitrogen atom is substituted by only one or at least one alkyl group having at least 14 carbon atoms, preferably 14 or 16 carbon atoms and
- more than 5%, preferably more than 7% in weight by weight of the total composition, of ammonium halides in which the nitrogen atom is substituted by only one or at least one alkyl group having at least 16 carbon atoms.

According to a preferred embodiment of this invention, the composition of ammonium halides comprises only C16-alkyl quaternary ammonium halide, more preferably ammonium chloride or bromide, in which the nitrogen atom of the ammonium group is substituted by only one or at least one alkyl group having 16 carbon atoms. Preferably, the composition of ammonium halides comprises C16-alkylbenzyl ammonium halide, preferably C16-alkylbenzyldimethyl ammonium halide, preferably BAK C16.

According to an embodiment of the present invention, the composition of ammonium halides comprises a C16-alkyl quaternary ammonium halide, in which the nitrogen atom of the ammonium group is substituted by two or three lower alkyl groups, preferably by two or three methyl groups.

Thus, in a preferred embodiment of the present invention, said oil-in-water emulsion comprises 0.0005% to 0.1% of C16-alkyl quaternary ammonium halide, in weight by weight of the emulsion.

According to a preferred embodiment, the emulsion of the invention comprises an oil phase, comprising mineral oil, castor oil, MCT, corn oil, olive oil, soybean oil or any suitable vegetable oil, preferably said oil phase comprises mineral oil, castor oil or MCT.

According to a preferred embodiment, the emulsion of the invention further comprises tyloxapol.

According to a preferred embodiment, the emulsion of the invention further comprises a tonicity agent such as for example glycerol, mannitol, sorbitol, sodium chloride; others surfactants such as poloxamer; and optionally at least one buffering agent such as for example citrate, phosphate, tris, borate, acetate, carbonate, borate-polyol complexes, histidine, gluconate and lactate.

In one preferred embodiment of the present invention, said emulsion comprises mannitol as tonicity agent.

In another preferred embodiment of the present invention, said emulsion comprises glycerol as tonicity agent.

Preferably, the emulsion includes 1% to 5% of oil phase, preferably of MCT castor oil or mineral oil, in weight by weight of the emulsion.

Preferably, the mineral oil phase is a mixture of heavy and light mineral oil.

The main droplet core is composed by 50% light mineral oil and 50% heavy mineral oil. Mineral oil is a mixture of refined liquid saturated aliphatic (C14-C18) and cyclic hydrocarbons obtained from petroleum. Light mineral oil is less viscous and has a lower specific gravity than heavy mineral oil. Heavy and light mineral oil are well known excipients, used in a variety of pharmaceutical formulations including oral, and topical (up to 95%) preparations. In ophthalmic ointments, mineral oil can be found as an excipient at concentrations of up to 60% A combination of light and heavy mineral oil in ophthalmology has been recognized by the US authorities as bearing emollient properties particularly adapted to dry eye treatment (21 CFR 349).

Preferably, the emulsion includes 0.1% to 1% of surfactants, such as tyloxapol and optionally poloxamer 188 and/or polysorbate 80 and/or tocopherol polyethylene glycol succinate and/or sorbitan monolaurate, in weight by weight of the emulsion.

Preferably, the emulsion comprises 0.3% of tyloxapol and optionally 0.1% of poloxamer 188, in weight by weight of the emulsion.

Preferably, the emulsion comprises 0.1% to 5% of tonicity agent (s), more preferably 0.5% to 4% and even more preferably 0.9% to 3.3%, in weight by weight of the emulsion.

In one embodiment, the emulsion comprises 0.1% to 5% of mannitol, more preferably 0.5% to 4% and even more preferably 0.9% to 3.3%, in weight by weight of the emulsion. In another embodiment, the emulsion comprises 0.1% to 2.5% of glycerol, more preferably 0.19% to 1.6%, in weight by weight of the emulsion.

In one preferred embodiment of the present invention, the emulsion comprises light and heavy mineral oil, tyloxapol, poloxamer 188, mannitol and cetalkonium chloride. Preferably, said emulsion comprises 0.5% of light mineral oil, 0.5% of heavy mineral oil, 0.3% of tyloxapol, 0.1% of poloxamer 188, 3.3% of mannitol, and 0.002% of cetalkonium chloride, in weight by weight of the emulsion.

In another preferred embodiment of the present invention, the emulsion comprises light and heavy mineral oil, tyloxapol, poloxamer 188, glycerol and cetalkonium chloride. Preferably, said emulsion comprises 0.5% of light mineral oil, 0.5% of heavy mineral oil, 0.3% of tyloxapol, 0.1% of poloxamer 188, 1.6% of glycerol, and 0.002% of cetalkonium chloride, in weight by weight of the emulsion.

According to a preferred embodiment of the invention, the emulsion is hypotonic with regards to the normal tears tonicity.

According to a preferred embodiment, the oil-in-water emulsion of the invention is less toxic than a solution comprising the same amount of the same C16-alkyl quaternary ammonium halide, in weight by weight of the solution. For example, the toxicity can be evaluated by a redness test or a Draize test as shown in the examples.

According to a preferred embodiment, the oil-in-water emulsion of the invention is less toxic than an emulsion comprising 0.01% to 0.1% of BAK in weight by weight of the emulsion, said BAK being a mixture of C12, C14 and C16-alkyl quaternary ammonium halide complying to US or European Pharmacopeia specifications.

According to a preferred embodiment, the oil-in-water emulsion of the invention does not induce redness in albino rabbit conjunctiva before administration of 9 drops of 50 μl, said drops being administrated each 5 minutes, preferably before administration of 11 drops, and more preferably before administration of 13 drops.

According to a first embodiment, the emulsion does not contain any active principle. In this embodiment, the emulsion is particularly useful as artificial tears, or for the treatment of dry eye condition such as for example Dry Eye Syndrome or Chronic Dry Eye Disease (CDED), both clinically known as keratoconjuctivitis sicca.

According to a second embodiment, the composition of the invention contains an active principle.

In one embodiment, said active principle is selected from secretagogues such as pilocarpine or celameline, immunosuppressive agents such as natural or synthetic cyclosporins, tacrolimus or sirolimus, mucin secretagogues such as 15(S)-HETE, ecabet or diquafosol, androgen mimetics, flaxseed oil supplements, steroids, agonists of adenosine A3 receptor, squalene, vitamin A; said active principle being preferably cyclosporine.

In another embodiment, said active principle is chosen among the active substances capable of having additional or synergistic therapeutic effects for treating KCS.

Preferably, said active principle can be selected in the group comprising astringents such as zinc sulfate, demulcents including cellulose derivatives, carboxymethylcellulose sodium, hydroxyethyl cellulose; hypromellose, methylcellulose, dextran 70, gelatin, polyethylene glycol 300, polyethylene glycol 400, polysorbate 80, propylene glycol, polyvinyl alcohol and povidone such as polyethylene glycol 6000, emollients such as lanolin preparations or oleaginous ingredients, vasoconstrictors such as naphazoline, ephedrine, tetrahydrozoline and phenylephrine salts.

In an embodiment of the invention, the oil-in-water emulsion is preserved.

In another embodiment of the invention, the oil-in-water emulsion is unpreserved; in an embodiment, the emulsion is packaged in unitary doses; in another embodiment, the emulsion is packaged in suitable multidose containers.

The present invention also relates to the oil-in-water emulsion as described here above, having a high viscosity, and being dispensed to the patient in the form of a gel suitable for ophthalmic use.

Another object of the present invention is also a medicament comprising the oil-in-water emulsion as described here above.

The present invention also relates to a kit for dry eye treatment comprising a first emulsion as described here above, which does not comprise an active principle, and a second emulsion which contains an active principle, preferably cyclosporine. According to an embodiment said second emulsion comprising an active principle is an emulsion according to the present invention.

According to another embodiment, said second emulsion comprising an active principle is any emulsion suitable for ophthalmic use.

Another object of this invention is a pre-concentrate of the therapeutic oil-in-water emulsion of the invention and a process for manufacturing said pre-concentrate.

According to this invention, a pre-concentrate is defined as an emulsion having an amount of oil higher than the amount of oil of the therapeutic emulsion administered to a patient. In a first embodiment, the amount of oil in the pre-concentrate is of at least 4% v/v. In a second embodiment, the amount of oil in the pre-concentrate is of at least 8% v/v. In a third embodiment, the amount of oil in the pre-concentrate is of at least 10% v/v., preferably of at least 20% v/v, more preferably of at least 30% v/v.

The pre-concentrate may be in a liquid form or in a gel form, or in any form suitable in view of its further dilution with water.

According to an embodiment, the pre-concentrate of ophthalmic oil-in-water emulsion according to the present invention may be sterilized, for example, by heat, such as by autoclaving, or by filtering or filtration, or by irradiation, or by gas sterilization. In another embodiment, the concentrate of the ophthalmic emulsion is prepared in an aseptic manner.

This invention also relates to a process for manufacturing a pre-concentrate of a therapeutic oil-in-water emulsion comprising the steps of emulsifying/mixing the oil phase with an aqueous phase and with surface-active component (s), wherein the optionally active principle is dissolved in the oil phase. The process for manufacturing said pre-concentrate comprises emulsifying an amount of oil with an aqueous phase and with suitable surfactants, in order to obtain an emulsion having an amount in oil higher than the amount in oil of the corresponding emulsion to be administered for therapeutic purposes.

Before beginning the manufacturing process, the therapeutic oil-in-water emulsion is designed, with a wished concentration of oil, the type of oil (suitable for ophthalmic use, such as for example mineral oil, castor oil, or MCT) the type of elements needed for emulsification such as surfactants for example, and optionally an active principle. The concentration of the concentrate is then decided, depending on the industrial volumes needed.

This invention also relates to a process for manufacturing a therapeutic oil-in-water emulsion comprising (1) manufacturing a pre-concentrate of an ophthalmic oil in water emulsion, said pre-concentrate having a content in oil of at least 4% v/v, preferably of 10% v/v or more, more preferably of 20% v/v or more, even more preferably of 30% v/v or more by emulsifying/mixing an oil suitable for ophthalmic use selected in the group comprising mineral oil, castor oil and MCT, said oil phase containing optionally one or more active principle and a C16-alkyl quaternary ammonium halide and with surface-active component (s), with an aqueous phase and then (2) diluting one volume of the resulting pre-concentrate with 2 to 50 volumes of water.

According to an embodiment, the emulsification is such that the droplet size or the distribution of the droplet size in the pre-concentrate is about the same as the droplet size or the distribution of the droplet size of the therapeutic oil-in-water emulsion. According to an embodiment, the diluting water may comprise additives selected from the group comprising tonicity agents, such as for example NaCl, glycerol or mannitol, viscosifying agents, buffering agents, preservatives, antioxidants or colorants.

According to an embodiment, the diluting water may also comprise a C16-alkyl quaternary ammonium halide.

Then, according to the invention, a pre-concentrate of this desired emulsion is produced by mixing the oil suitable for ophthalmic use, with an aqueous phase and with surface-active component (s); the average hydrophilic-lipophilic balance (HLB) of the surface-active component (s) may advantageously be about equal to the HLB or average HLB emulsion requirement of the oil or oils used in the present compositions.

An advantage of this invention is to produce large volumes of emulsions without having to scale-up the emulsifying process.

This invention relates to a process for manufacturing a therapeutic oil-in-water emulsion according to the invention, comprising manufacturing a concentrate according to the above-mentioned process and then diluting said concentrate, by mixing 1 volume of concentrate with 2 to 50 volumes of water, to obtain a final therapeutic emulsion having an oil content of 5% v/v of less, preferably of 3% v/v or less, more preferably of 2% v/v or less, even more preferably of 1% v/v or less.

This invention also relates to a method for the treatment of ocular diseases or conditions consisting in the administration to a patient of an ophthalmic emulsion prepared from a pre-concentrate, according to the above described process.

The invention also relates to oil-in-water emulsions obtainable by the process of the invention, i.e. by manufacturing a concentrate including optionally an active principle, and then diluting said concentrate with 2 to 50 volumes of water, said water optionally comprising additives, such as for example tonicity agents, viscosifying agents, buffering agents, preservatives, antioxidants or colorants.

One advantage of the invention is that the oil-in-water emulsions obtained by dilution of the concentrates are formed with reduced energy input.

The following examples and figures illustrate the invention and should not be interpreted in any way as reducing the scope of this invention.

EXAMPLES

All concentrations in the emulsion formula are expressed in weight/weight of the entire formulation, unless stated differently.

Example 1

Reduced Toxicity of Quaternary Amines when Incorporated into Emulsions

Materials and Methods
Material
1. Solution at 0.02% BAK (BAK So)

| Excipients | Z01SOL472 |
| --- | --- |
| BAK US | 0.02 |
| NaCl | 0.612 |
| Tris Buffer 5 mM pH 7.1 | 0.069% Tris HCl |
| | 0.006% Tris Base |
| Water | Ad 100 |

2. Emulsion at 0.02% BAK (BAK Em)

| Excipients | Z01EM471 |
| --- | --- |
| Mineral oil heavy | 0.500 |
| Mineral oil light | 0.500 |
| Tyloxapol | 0.300 |
| BAK US | 0.02 |
| Tris Buffer 5 mM pH 7.1 | 0.069% Tris HCl |
| | 0.006% Tris Base |
| Poloxamer 188 | 0.100 |
| Glycerol | 1.6 |
| Water (up to 100) | Ad 100 |

3. Solution at 0.002% CKC(CKC Sol)

| Excipients | Z01SOL473 |
| --- | --- |
| CKC | 0.002 |
| NaCl | 0.626 |
| Tris Buffer 5 mM pH 7.1 | 0.069% Tris HCl |
| | 0.006% Tris base |
| Water | Ad 100 |

4. Emulsion at 0.002% CKC(CKC Em)

| Excipients | Z01EM264 |
| --- | --- |
| Mineral oil heavy | 0.500 |
| Mineral oil light | 0.500 |
| Tyloxapol | 0.300 |
| CKC | 0.002 |
| Tris Buffer 5 mM pH 7.1 | 0.069% Tris HCl |
| | 0.006% Tris Base |
| Poloxamer 188 | 0.100 |
| Glycerol | 1.6 |
| Water (up to 100) | Ad 100 |

5. PBS

Methods:

Albino rabbits were administrated with 1 drop (50 μl) each 5 minutes, for 15 times.

Results

Evaluation of Toxicity by Time of Redness and DRAIZE Test Items Analyzed at H4 and D1.

Figure 1:
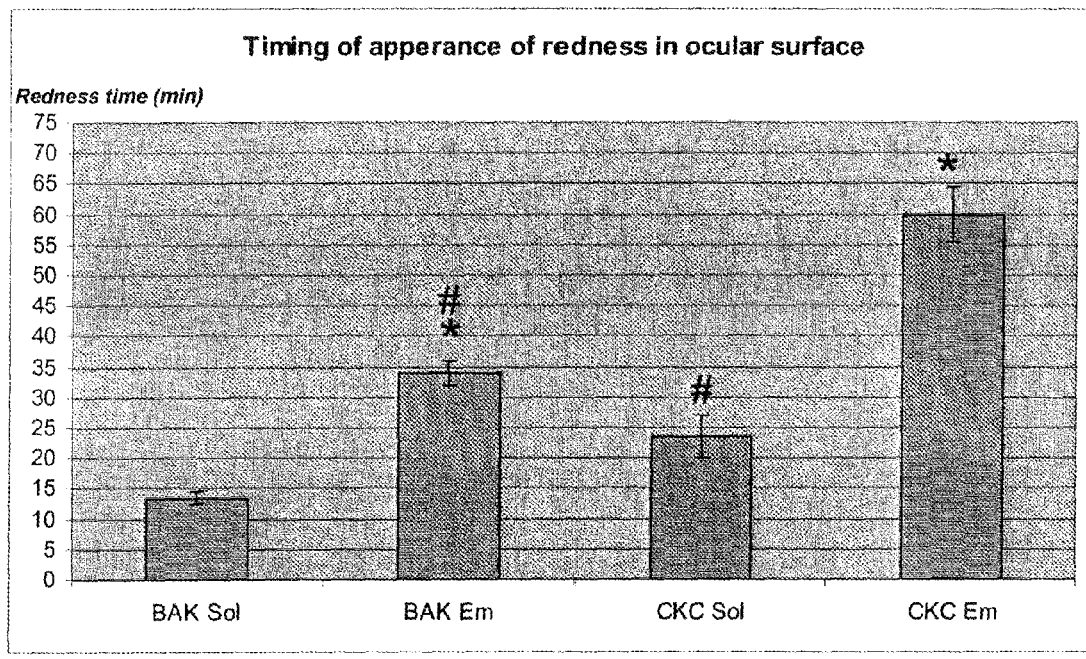
FIG. 1 refers to the timing of appearance of redness in ocular surface.

The time of the beginning of the redness in conjunctiva following the 15 times of instillations was evaluated (FIG. 1). PBS did not induce any redness during all instillation period (data not shown). BAK Sol induced conjunctival redness very fast, about 10 to 15 minutes after the first instillation (after 2-3 drops). BAK Em, CKC Sol-instilled groups showed redness at about 25-35 minutes after the first instillation of eye drops (after 5-7 drops). CKC Em presented a visible redness at almost the end of the experimentation: 60 to 65 minutes after the first instillation (after 12-13 drops).

Figure 2:
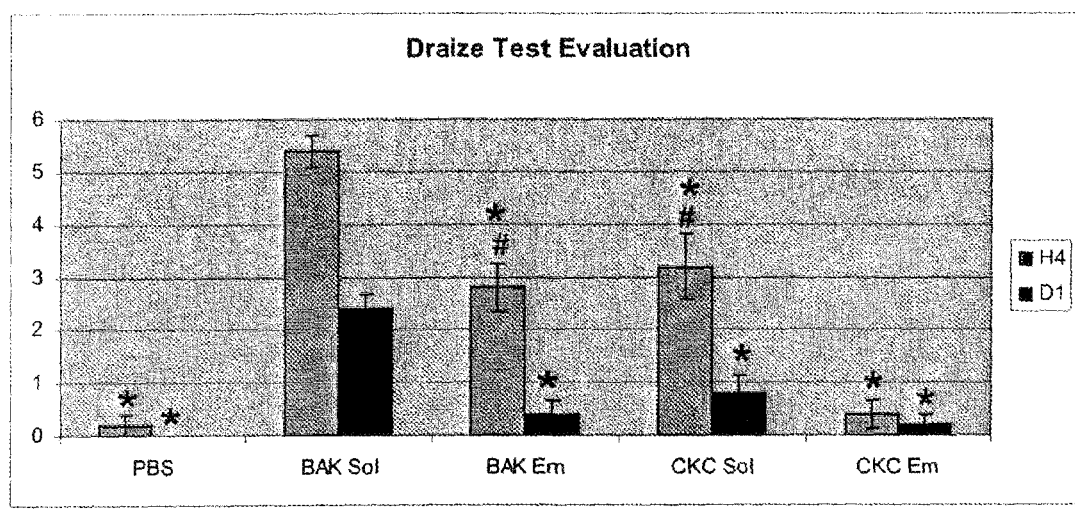
FIG. 2 refers to Draize Test evaluation.

Draize Test clearly showed that at four hours (H4) after the last instillation the ocular irritation was the most important in BAK Sol-instilled group, which was higher than BAK Em and CKC Sol groups (with no difference between these two groups). BAK Sol, BAK Em, CKC Sol all showed higher ocular irritation than CKC Em, which presented no difference with PBS-instilled group (FIG. 2).

One day after the administrations (D1), PBS, BAK Em, CKC Sol and CKC Em all returned to normal aspect without difference among them. But BAK Sol still induced more important ocular irritation than all other groups ($P<0.0001$).

Example 2

Stability of the Emulsions of the Invention

1. Emulsions Composition

Some emulsions are described below:

| Composition | Z01EM206 | Z01EM209 |
|---|---|---|
| MCT | 2% | 2% |
| Tyloxapol | 0.3% | 0.3% |
| BAK C16 (CKC) | 0.02% | 0.025 mM |
| Poloxamer 188 | 0.1% | 0.1% |
| Glycerol | 2.25% | 2.25% |
| Water | qsp 100 | qsp 100 |

| Composition | Z01EM393-4 | Z01EM395-6 |
|---|---|---|
| MCT | 1-2% | 1-2% |
| Tyloxapol | 0.3% | 0.3% |
| PG | 0.4% | — |
| Mannitol | — | 0.9% |
| Glycerol | 1% | 1% |
| Cetalkonium chloride (CKC) | 0.01% | 0.01% |
| Water | Up to 100% | Up to 100% |

2. Emulsions Preparation

The oily and the water phases of the emulsion, which might contain or not an active principle, may be separately heated to an appropriate temperature. This temperature may be the same in both cases. Surfactants might be dissolved in the oil, water phase or in both. A first coarse emulsion is generated by magnetic stirring, and the droplet size is reduced by high shear mixing, high pressure homogenization, or both.

The oil-in-water emulsions of the present invention can be sterilized after preparation using heat, for example, autoclave steam sterilization.

3. Impact of Chain Length on Emulsions Characteristics a) Emulsion Droplet Size

The mean diameter of the oil droplets is determined by dynamic light scattering using a High Performance Particle Sizer type HPPS 5001 (Malvern Instruments, Worcestershire, UK). Measurements are performed at 25° C. following dilution of the emulsion in double distilled water.

TABLE 1

Emulsions droplet size values (nm)
Emulsions of Table 1 and Table 2 contain 2% MCT, 0.3% Tyloxapol and 0.1% Poloxamer 188 and 2.25% glycerol and compositions of BAK; concentrations of BAK range from 0.001% to 0.1% in weight to the weight of the emulsion.

| | 0.001% | 0.0025% | 0.005% | 0.01% | 0.02% | 0.04% | 0.1% |
|---|---|---|---|---|---|---|---|
| BAK C12 | — | — | 198 | 263 | 230 | 225 | 180 |
| BAK C14 | — | 204 | 190 | 190 | 155 | 238 | 185 |
| BAK C16 | 220 | 210 | 148 | 180 | 155 | 188 | 183 |

| Composition | Z01EM419 | Z01EM264 | Z01EM387 | Z01EM418(a) | Z01EM418(b) |
|---|---|---|---|---|---|
| Light mineral oil | 0.5% | 0.5% | 0.5% | 0.5% | 0.5% |
| Heavy mineral oil | 0.5% | 0.5% | 0.5% | 0.5% | 0.5% |
| Tyloxapol | 0.3% | 0.3% | 0.3% | 0.3% | 0.3% |
| Poloxamer 188 | 0.1% | 0.1% | — | — | — |
| PG | — | — | 0.19% | — | — |
| PEG 300 | — | — | 0.19% | — | — |
| PEG 400 | — | — | 0.19% | — | — |
| Mannitol | 3.3% | — | 2% | 2.5% | 2.9% |
| Glycerol | — | 1.6% | 0.19% | 0.19% | — |
| Cetalkonium chloride (CKC) | 0.002% | 0.002% | 0.002% | 0.002% | 0.002% |
| Tromethamine | 0.006% | 0.006% | — | — | — |
| Tris HCl | 0.071% | 0.071% | — | — | — |
| Water | Up to 100% | Up to 100% | Up to 100% | Up to 100% | Up to 100% | b) Emulsion Zeta Potential

The stability of the cationic emulsions of the invention may be evaluated by determining their ability to keep a positive and stable zeta potential overtime. Measurement of zeta potential is commonly used to assess the stability of colloidal systems. Indeed, zeta potential of the oil-in-water emulsion is representative of the electronic charges present at the surface of the oil droplets. When oil droplets are positively charged, droplets undergo electrostatic repulsions, avoiding their coalescence. Thus, retaining a stable positive zeta potential overtime for a cationic emulsion illustrates its stability.

The zeta potential of emulsions comprising increasing concentrations of different quaternary ammonium compounds (BAK C12, BAK C14 and BAK C16) was thus measured.

Zeta potential can be measured by a zetameter such as Zetasizer 2000, Malvern Instruments Ltd, UK. The zeta potential of the emulsion droplet surface is determined by electrophoretic mobility. Measurements are performed at 25° C. following dilution at 1:250 of the emulsion in double distilled water. The electrophoretic mobility is converted into zeta potential values through the Smoluchowsky equation.

Results are presented in Table 2 below and graphically represented in FIG. 3.

TABLE 2

Emulsions zeta potential values (mV)

| | 0.001% | 0.0025% | 0.005% | 0.01% | 0.02% | 0.04% | 0.1% |
|---|---|---|---|---|---|---|---|
| BAK C12 | — | — | −6.9 | +4.2 | +7.9 | +16.8 | +23.8 |
| BAK C14 | — | +11.4 | +19.6 | +22.9 | +28.4 | +39.3 | +44.5 |
| BAK C16 | +16.2 | +24.4 | +31.4 | +36.7 | +44.1 | +47.2 | +48.9 |

Figure 3:
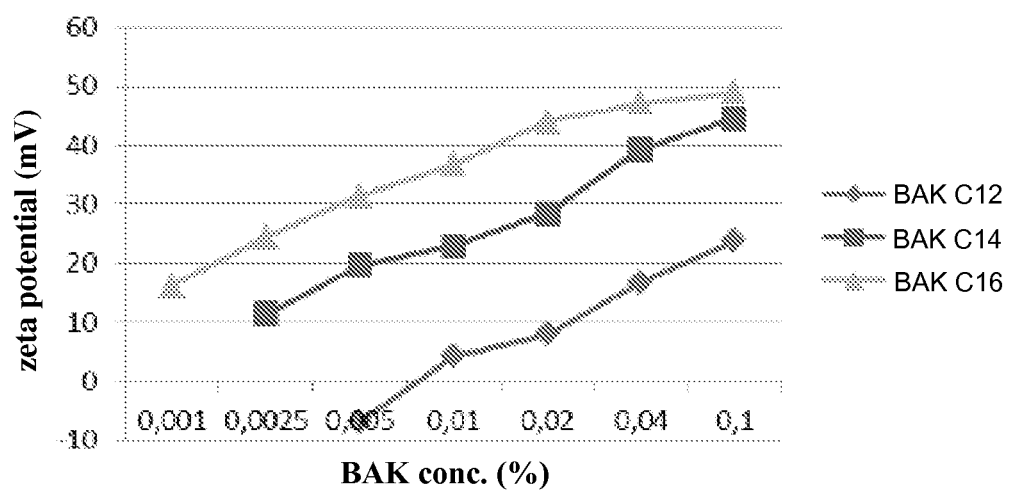
FIG. 3 refers to the zeta potential of emulsions of example 2, part 3.b) in function of BAK concentration.

Results presented in Table 2 and FIG. 3 evidence that positive charges are attained at lower concentrations when the chain length of the quaternary ammonium compound is increased. They also suggest a preferential partition of more lipophilic chain (long alkyl chain) within the oil droplet surface.

CKC (BAK C16) is thus proved to have a greater cationic power than a quaternary ammonium compound with smaller alkyl chain length. In other words, emulsions comprising CKC display a higher zeta potential than those comprising the same amount of BAK US. Therefore, BAK US and CKC are not interchangeable, which is confirmed by data of example 3.

c) Emulsion Stability Overtime

The stability of the emulsions can be evaluated by the evolution of their aspect, with a visual score with a visual score going from 13—best aspect to 1—total phase separation.

It can be observed from the following table that, at equimolar concentration, longer (more lipophilic) chain length QA results in more stable emulsion.

| Type and conc. of QA | After preparation (T0) | Following 3 months at 40° C. |
|---|---|---|
| 0.25 mM BAK C12 | 12 | 2 |
| 0.25 mM BAK C14 | 13 | 7 |
| 0.25 mM BAK C16 | 13 | 9 |
| 0.5 mM BAK C12 | 10 | 2 |
| 0.5 mM BAK C14 | 13 | 7 |
| 0.5 mM BAK C16 | 11 | 9 |

Example 3

Comparison of the Stability of Emulsions Comprising Either CKC or BAK

The stability of emulsions containing 0.002% w/w of CKC and 0.002% w/w of BAK was compared. Compared emulsions have following compositions:

| | 0.002% CKC emulsion | 0.002% BAK emulsion |
|---|---|---|
| Light mineral oil | 0.5% | 0.5% |
| Heavy mineral oil | 0.5% | 0.5% |
| CKC | 0.002% | \ |
| BAK US | \ | 0.002% |
| Tyloxapol | 0.3% | 0.3% |
| Poloxamer 188 | 0.1% | 0.1% |
| Glycerol | 1.6% | 1.6% |
| Tris buffer 5 mM pH 7.1 | 0.071% Tris HCl 0.006% Tris Base | 0.071% Tris HCl 0.006% Tris Base |
| Water | up to 100% | up to 100% |

The zeta potential of the two emulsions was followed overtime using thermal stress test conditions. Thermal stress tests enable to accelerate commonly used stability tests. In the thermal stress test used therein, zeta potential of the emulsion was measured at T=0, i.e. as soon as the emulsion has been prepared. Glass vials of 10 mL effective capacity containing 5-10 mL of emulsion and sealed under nitrogen atmosphere were stored at 80° C. Then, at T=7 days and 14 days, the zeta potential was measured. Results of zeta potential measurement, in mV, are given in the table below:

| | T0 | T = 7 days | T = 14 days |
|---|---|---|---|
| 0.002% CKC emulsion | +21.2 | — | +22.6 |
| 0.002% BAK US emulsion | +6.73 | −9.66 | −15.8 |

It clearly appears that the emulsion containing 0.002% w/w of BAK does not keep a positive and stable zeta potential overtime, contrary to the emulsions of the invention containing 0.002% w/w of CKC.

Considering the results reported above, it is clear that CKC and BAK US are not interchangeable.

The invention claimed is:
1. An oil-in-water emulsion comprising:
   an oil phase comprising mineral oil, castor oil or medium chain triglycerides;
   0.0005% to 0.1% w/w of ammonium halide, cetalkonium chloride being the sole ammonium halide of the emulsion; and
   0.1% to 1% w/w of surfactant selected from tyloxapol, poloxamer 188, or a mixture thereof.
2. The oil-in-water emulsion according to claim 1, wherein the mineral oil is a mixture of heavy and light mineral oil.
3. The oil-in-water emulsion according to claim 1, further comprising buffering agents and/or at least one tonicity agent.
4. The oil-in-water emulsion according to claim 3, wherein the tonicity agent is mannitol.
5. The oil-in-water emulsion according to claim 3, wherein the tonicity agent is glycerol.
6. The oil-in-water emulsion according to claim 1, said emulsion having a positive zeta potential.
7. The oil-in-water emulsion according to claim 1, said emulsion having a droplet size of 100 to 500 nm.

8. The oil-in-water emulsion according to claim 1, said emulsion comprising light and heavy mineral oil, tyloxapol, poloxamer 188, mannitol and cetalkonium chloride.

9. The oil-in-water emulsion according to claim 1, said emulsion comprising light and heavy mineral oil, tyloxapol, poloxamer 188, glycerol and cetalkonium chloride.

10. The oil-in-water emulsion according to claim 1, said emulsion being hypotonic, relative to normal tears.

11. The oil-in-water emulsion according to claim 1, wherein said emulsion is in the form of a gel suitable for ophthalmic use.

12. The oil-in-water emulsion according to claim 1, being less toxic than a solution comprising the same amount of cetalkonium chloride, in weight by weight of the solution.

13. The oil-in-water emulsion according to claim 1, further comprising an active principle.

14. The oil-in-water emulsion according to claim 13, wherein the active principle is cyclosporine.

15. A medicament comprising the oil-in-water emulsion according to claim 1.

16. A method for preparing an ophthalmic composition for dry eye treatment, comprising preparing the emulsion according to claim 1 in a gel form.

17. A kit for dry eye treatment comprising a first emulsion according to claim 1 and a second emulsion containing cyclosporine.

18. The medicament according to claim 15, wherein said emulsion is in a gel form suitable for ophthalmic use.

\* \* \* \* \*